(12) United States Patent
Yamada et al.

(10) Patent No.: US 6,723,682 B2
(45) Date of Patent: Apr. 20, 2004

(54) WATER DISPERSIBLE GRANULES

(75) Inventors: Masahiro Yamada, Minoo (JP);
Tadashi Otsuka, Osaka (JP)

(73) Assignee: Sumitomo Chemical Company, Limited, Osaka (JP)

( * ) Notice: Subject to any disclaimer, the term of this patent is extended or adjusted under 35 U.S.C. 154(b) by 0 days.

(21) Appl. No.: 10/251,810

(22) Filed: Sep. 23, 2002

(65) Prior Publication Data

US 2003/0064896 A1 Apr. 3, 2003

(30) Foreign Application Priority Data

Sep. 26, 2001 (JP) ........................................ 2001-293411

(51) Int. Cl.$^7$ ........................ A01N 25/130; A01N 43/38
(52) U.S. Cl. ........................ 504/132; 504/128; 504/130; 504/132; 504/134; 504/225; 504/286; 504/363; 544/105
(58) Field of Search ................................ 504/225, 286, 504/363, 128, 130, 132, 134; 544/105

(56) References Cited

U.S. PATENT DOCUMENTS

| | | |
|---|---|---|
| 4,640,707 A | 2/1987 | Nagano et al. |
| 4,867,972 A | 9/1989 | Girardeau et al. |
| 6,534,444 B1 * | 3/2003 | Sievernich et al. .......... 504/128 |
| 6,559,098 B1 * | 5/2003 | Bratz et al. ................. 504/116 |
| 2001/0044382 A1 * | 11/2001 | Reugg ........................ 504/139 |

FOREIGN PATENT DOCUMENTS

| | | |
|---|---|---|
| JP | 5-43402 A | 2/1993 |
| JP | 6-76283 B2 | 9/1994 |
| JP | 7-126106 A | 5/1995 |

OTHER PUBLICATIONS

Wood, Alan Internet: http://www.hclrss.demon.co.uk/flumioxazin.html.*

United States Environmental Protection Agency, Flumioxazin: Pesticide Tolerances, Apr. 18, 2001, Federal Register (vol. 66, No. 75, p. 19870–19879) DOCID: fr18ap01–13.*

United States Environmental Protection Agency (Office of Prevention, Pesticides, and Toxic Substances), Flumioxazin: Pesticide Fact Sheet, Apr. 12, 2001, USEPA Pesticide Fact Sheets.*

* cited by examiner

Primary Examiner—Sabiha Qazi
(74) Attorney, Agent, or Firm—Sughrue Mion, PLLC

(57) ABSTRACT

Water dispersible granules comprising (a) N-(7-fluoro-3,4-dihydro-3-oxo-4-prop-2-ynyl-2H-1,4-benzoxazin-6-yl) cyclohex-1-ene-1,2-dicarboximide, (b-1) an arylsulfonic acid formalin condensate or its salt, (b-2) a polycarboxylate surfactant and (c) a mineral carrier have a good disintegrability in water and can be produced in good yield.

8 Claims, No Drawings

WATER DISPERSIBLE GRANULES

FIELD OF THE INVENTION

The present invention relates to water dispersible granules of N-(7-fluoro-3,4-dihydro-3-oxo-4-prop-2-ynyl-2H-1,4-benzoxazin-6-yl)cyclohex-1-ene-1,2-dicarboximide (flumioxazin).

BACKGROUND ART

Flumioxazin is a herbicidal compound described in U.S. Pat. No. 4,640,707. This invention provides novel water dispersible granules containing flumioxazin as an active ingredient.

Water dispersible granules are usually applied to fields after diluted 20–10000 times with water. They are easy-handling formulation because users can measure by volume without powdering. However when disintegrability of the water dispersible granules in water is not good, it causes ununiformity of the active ingredient in the dilution, resulting in uniform application . The ununiform application causes decrease of effect at the place the dosage is small and it also causes phytotoxicity at the place agglomerating particles which are not disintegrated perfectly are adhered to. As a result, the quality of the water dispersible granules are remarkably bad. In order to avoid these potential problems, it may be needed to increase the dosage or the number of the applications of the pesticide or treat for preventing phytotoxicity to cultivated plants. It was troublesome because it needs extra costs or labors.

Further, when granulated particles tend to agglomerate just after granulation process , aggregation is produced before drying process, and as a result, the yield of the formulation lowers. It has been desired to solve the problem and to provide water dispersible granules which can be manufactured easily in good yield.

SUMMARY OF THE INVENTION

The present invention provides water dispersible granules comprising (a) flumioxazin as an active ingredient, (b-1) arylsulfonic acid formalin condensate or its salt, (b-2) a polycarboxylate surfactant and (c) a mineral carrier. Further, it also provides water dispersible granules comprising (a) flumioxazin, (b-1) an arylsulfonic acid formalin condensate or its salt, (b-2) a polycarboxylate surfactant, (b-3) a laurylsulfuric acid salt or alkylarylsulfonic acid salt and (c) a mineral carrier.

The water dispersible granules provided by the present invention have a good disintegrability in water. Further, the water dispersible granules can be produced in good yield.

DETAILED DESCRIPTION OF THE INVENTION

In the present invention, the flumioxazin is used as an active ingredient. Flumioxazin is available on the market and it can also be prepared according to the description in U.S. Pat. No. 4,640,707.

The content of the flumioxazin is usually 0.1–80% by weight, preferably 1–60% by weight based on the present water dispersible granules.

It is preferable that the flumioxazin is pulverized to 1–10 $\mu$m in advance in view of the formulation properties such as suspensibility. Examples of the arylsulfonic acid formalin condensate include phenylsulfonic acid formalin condensate, tolylsulfonic acid formalin condensate, naphthalenesulfonic acid formalin condensate and alkylnaphthalenesulfonic acid formalin condensate. Examples of the salts of the arylsulfonic acid formalin condensate include sodium salts, calcium salts and potassium salts of the above-mentioned arylsulfonic acid formalin condensates. In the present invention, the arylsulfonic acid formalin condensate or salts thereof can be utilized solely or as a mixture of two or more at any mixing ratio. In the present invention, the polycarboxylate surfactant means alkali or alkaline earth metal salt of copolymer, wherein the monomer unit of the copolymer is unsaturated carboxylic acid with another unsaturated carboxylic acid or olefin. Typical examples of the polycarboxylate surfactant include sodium and calcium salts of copolymer of maleic acid with diisobutylene, maleic acid with isobutylene, acrylic acid with itaconic acid and maleic acid with styrene.

The total content of the arylsulfonic acid formalin condensate or its salt and the polycarboxylate surfactant is usually 0.1–70% by weight, preferably 1–40% by weight, more preferably 3–20% by weight based on the present water dispersible granules. The weight ratio of the arylsulfonic acid formalin condensate or its salt to the polycarboxylate surfactant is preferably 1:1 to 10:1.

Examples of the mineral carrier include kaolin clay, diatomaceous earth, terra alba, talc, calcium carbonate and attapulgite clay. Among them, kaolin clay and talc are preferable. Kaolin clay is a clay mineral containing 50% by weight or more of kaolin (kaolinite, nacrite, dickite, halloysite, hydrated halloysite, etc.) as its main component. Further, talc is produced by pulverizing talc mineral and comprises magnesium silicate or acid magnesium metasilicate as a main component. The content of the mineral carrier is usually 1–70% by weight, preferably 3–60% by weight, more preferably 10–50% by weight in the present water dispersible granules.

The present water dispersible granules optionally comprise the other anionic surfactant such as laurylsulfuric acid salts, alkylarylsulfonic acid salts, alkylnaphthalenesulfonic acid salts, ligninsulfonic acid salts, dialkylsulfosuccinate, polyoxyethylenealkyl aryl ethersulfate salts and fatty acid salts; nonionic surfactant such as polyoxyethylenealkyl ethers, polyoxyethylenealkyl phenyl ethers, polyoxyethylenestyryl phenyl ethers, polyoxyethylenealkyl esters, sorbitan alkyl esters and polyoxyethylenesorbitan alkyl esters; cationic surfactant; and zwitter ionic surfactant. Among them, laurylsulfuric acid salts and alkylarylsulfonic acid salts are preferably used. Examples of the laurylsulfuric acid salts include sodium salt, calcium salt, ammonium salt and alkanolamine salts and examples of the alkylarylsulfonic acid salts include calcium dodecylbenzenesulfonate, sodium dodecylbenzenesulfonate and sodium methylnaphthalenesulfonate. When said surfactant is utilized, the content is usually 0.1–10% by weight in the present water dispersible granules.

Further, the present water dispersible granules can contain a solvent, stabilizer, synergist, coloring agent, perfume, builder and so on, unless its addition makes the effect of the present invention lost.

The present water dispersible granules are practically applied after dilution with water by an appropriate ratio. The dilution rate is usually 20 to 10000 times, but it can be varied by content of the active ingredient in the present water dispersible granules, kind of the objected weeds, objected crops, timing of the application, application method and so on.

The present water dispersible granules can be prepared, for example, by the followings.

Namely, the present water dispersible granules can be prepared by mixing flumioxazin, the arylsulfonic acid formalin condensate or its salt, the polycarboxylate surfactant, the mineral carrier, and optionally the other surfactant and so on, adding water thereto, kneading, granulating with extruder having 0.5–1.5 mm φ screen, drying and optionally treating with spherizer or sizing before or after drying. The flumioxazin may be used after pulverizing.

The particle diameter of the present water dispersible granules is usually 200–2000 μm, preferably 500–1180 μm.

EXAMPLES

The present invention will be explained by production examples and test examples in detail below, but the present invention should not be limited to the examples.

In the following examples, part(s) means part(s) by weight unless it is specifically mentioned.

Production Example 1

To 51 parts of flumioxazin pulverized with an air mill to 4 μm of average particle diameter, 4 parts of sodium salt of copolymer of maleic acid with diisobutylene (commercial name: DEMOL EP powder, produced by Kao Corp.), 6 parts of sodium salt of arylsulfonic acid formalin condensate (commercial name: DEMOL SNB, produced by Kao Corp.), 2 parts of sodium laurylsulfate (commercial name: EMAL 10 powder, produced by Kao Corp.) and 37 parts of kaolin clay (commercial name: Shokozan A clay, produced by Shokozan Kogyosho) were added and mixed with a juice mixer for 5 minutes. After that, the mixture was kneaded with 16 parts of water in a mortar for 5 minutes. The kneaded mixture was granulated with extruder having 0.7 mm φ screen (Hatashiki granulator produced by Hata Seisakusho), treated with a spherizer, dried at 60° C. for 12 minutes and screened to provide the present water dispersible granules having 500–1180 μm of the particle diameter.

Production Example 2

To 51 parts of flumioxazin pulverized with an air mill to 4 μm of average particle diameter, 1.5 parts of sodium salt of copolymer of maleic acid with diisobutylene (commercial name: DEMOL EP powder, produced by Kao Corp.), 3.5 parts of sodium salt of arylsulfonic acid formalin condensate (commercial name: DEMOL SNB, produced by Kao Corp.), 2 parts of sodium laurylsulfate (commercial name: EMAL 10 powder, produced by Kao Corp.) and 42 parts of kaolin clay (commercial name: Shokozan A clay, produced by Shokozan Kogyosho) are added and mixed with a small nauta mixer (Labomixer LV-0, produced by Hosokawamicron) for 10 minutes. After that, the mixture is kneaded with 16 parts of water in a kneader (KDHJ-10 type, produced by Fujipaudal) for 5 minutes. The kneaded mixture is granulated with extruder having 0.7 mm φ screen (TWIN-DOME GRAN, produced by Fujipaudal), dried at 60° C. for 12 minutes, treated with a spherizer, and screened to provide the present water dispersible granules having 500–1180 μm of the particle diameter.

Production Example 3

To 51 parts of flumioxazin pulverized with an air mill to 4 μm of average particle diameter, 1.5 parts of sodium salt of copolymer of maleic acid with diisobutylene (commercial name: DEMOL EP powder, produced by Kao Corp.), 3.5 parts of sodium salt of arylsulfonic acid formalin condensate (commercial name: DEMOL SNB, produced by Kao Corp.), 2 parts of sodium laurylsulfate (commercial name: EMAL 10 powder, produced by Kao Corp.) and 42 parts of talc are added and mixed with a small nauta mixer (Labomixer LV-0, produced by Hosokawamicron) for 10 minutes. After that, the mixture is kneaded with 16 parts of water in a kneader (KDHJ-10 type, produced by Fujipaudal) for 5 minutes. The kneaded mixture is granulated with extruder having 0.7 mm φ screen (TWIN-DOME GRAN, produced by Fujipaudal), dried at 60° C. for 12 minutes, treated with a spherizer, and screened to provide the water dispersible granules of the present invention having 500–1180 μm of the particle diameter.

Production Example 4

By the same procedure as Production example 1 except that naphthalenesulfonic acid formalin condensate is used in place of the sodium salt of arylsulfonic acid formalin condensate, obtained are the water dispersible granules of the present invention.

Reference Example 1

By the same procedure as Production example 1 except that the sodium salt of arylsulfonic acid formalin condensate was not used and that the used amount of the sodium salt of copolymer of maleic acid with diisobutylene was 5 parts, obtained were water dispersible granules having 500–1180 μm of the particle diameter.

Reference Example 2

By the same procedure as Production example 1 except that the sodium salt of copolymer of maleic acid with diisobutylene was not used and that the used amount of the sodium salt of arylsulfonic acid formalin condensate was 5 parts, obtained was water dispersible granules having 500–1180 μm of the particle diameter.

Test Example 1

A 250 ml-volume cylinder with a stopper containing 250 ml of 3° hard water was set in a thermostat of 20° C. Each 500 mg of the water dispersible granules given in table 1 was added to the cylinder, which was then turned upside down. This upside-down turning was repeated at a rate of once per two seconds. The number of the repetition of the upside-down turning was observed to complete disintegration of the water dispersible granules.

The results are given in table 1.

Test Example 2

When sieved with 500 μm and 1180 μm in the production of the water dispersible granules given in table 1, each weight of the samples on or under the sieve was measured and the yield of the water dispersible granules was calculated by the formula below.

The results are given in table 1.
Yield of the water dispersible granules of 500–1180 μm=100B/(A+B+C)

A: Sample weight under 500 μm seive
B: Sample weight on 500 μm seive and under 1180 μm seive
C: Sample weight on 1180 μm seive

TABLE 1

| Water dispersible granules | Turning number | Yield of the water dispersible granules of 500–1180 μm |
|---|---|---|
| Production example 1 | 7 | 92% |
| Reference example 1 | 11 | 89% |
| Reference example 2 | 9 | 70% |

We claim:
1. Water dispersible granules which comprise (a) N-(7-fluoro-3,4-dihydro-3-oxo-4-prop-2-ynyl-2H-1,4-benzoxazin-6-yl)cyclohex-1-ene-1,2-dicarboximide, (b-1)

an arylsulfonic acid formalin condensate or its salt, (b-2) a polycarboxylate surfactant and (c) a mineral carrier.

2. Water dispersible granules according to claim 1, wherein the ratio of (b-1) to (b-2) is 1:1 to 10:1.

3. Water dispersible granules according to claim 2, wherein the content of (a) is 0.1–80% by weight, the total content of (b-1) and (b-2) is 0.1–70% by weight and the content of (c) is 1–70% by weight.

4. Water dispersible granules according to claim 3, wherein the mineral carrier is kaolin clay or talc.

5. Water dispersible granules according to claim 1, which comprise (a) N-(7-fluoro-3,4-dihydro-3-oxo-4-prop-2-ynyl-2H-1,4-benzoxazin-6-yl)cyclohex-1-ene-1,2-dicarboximide, (b-1) an arylsulfonic acid formalin condensate or its salt, (b-2) a polycarboxylate surfactant, (b-3) a laurylsulfuric acid salt or alkylarylsulfonic acid salt and (c) a mineral carrier.

6. Water dispersible granules according to claim 5, wherein the ratio of (b-1) to (b-2) is 1:1 to 10:1.

7. Water dispersible granules according to claim 6, wherein the content of (a) is 0.1–80% by weight, the total content of (b-1) and (b-2) is 0.1–70% by weight, the content of (b-3) is 0.1 to 10% by weight and the content of (d) is 1–70% by weight.

8. Water dispersible granules according to claim 7, wherein the mineral carrier is kaolin clay or talc.

* * * * *